(12) United States Patent
Mody

(10) Patent No.: US 7,306,764 B2
(45) Date of Patent: Dec. 11, 2007

(54) WETNESS INDICATOR

(75) Inventor: Nita Mody, Houston, TX (US)

(73) Assignee: Precision Laminates Inc., Houston, TX (US)

( * ) Notice: Subject to any disclaimer, the term of this patent is extended or adjusted under 35 U.S.C. 154(b) by 230 days.

(21) Appl. No.: 10/806,711

(22) Filed: Mar. 23, 2004

(65) Prior Publication Data

US 2004/0191118 A1    Sep. 30, 2004

Related U.S. Application Data

(60) Provisional application No. 60/456,578, filed on Mar. 24, 2003.

(51) Int. Cl.
*G01N 21/00* (2006.01)

(52) U.S. Cl. ............... 422/58; 422/56; 422/57; 604/367

(58) Field of Classification Search ........... 422/56–58; 604/367

See application file for complete search history.

(56) References Cited

U.S. PATENT DOCUMENTS

| | | | |
|---|---|---|---|
| 3,675,654 A | 7/1972 | Baker et al. | |
| 3,731,685 A | 5/1973 | Eidus | |
| 4,022,211 A | 5/1977 | Timmons et al. | |
| 4,036,360 A * | 7/1977 | Deffeyes ............ | 206/204 |
| 4,192,311 A | 3/1980 | Felfoldi | |
| 4,231,370 A | 11/1980 | Mroz et al. | |
| 4,287,153 A | 9/1981 | Towsend | |
| 4,705,513 A | 11/1987 | Sheldon et al. | |
| 4,743,238 A | 5/1988 | Colon et al. | |
| 5,035,691 A | 7/1991 | Zimmel et al. | |
| 5,066,711 A | 11/1991 | Colon et al. | |
| 5,089,548 A | 2/1992 | Zimmel et al. | |
| 5,167,652 A * | 12/1992 | Mueller ............ | 604/385.01 |
| 5,354,289 A | 10/1994 | Mitchell et al. | |
| 5,690,624 A | 11/1997 | Sasaki et al. | |
| 6,096,299 A * | 8/2000 | Guarracino et al. ....... | 424/76.1 |
| 2001/0037101 A1* | 11/2001 | Allan et al. ........... | 604/368 |
| 2001/0049513 A1* | 12/2001 | Neading et al. ......... | 604/361 |

FOREIGN PATENT DOCUMENTS

| | | | | |
|---|---|---|---|---|
| JP | 59106501 A | * | 6/1984 | |
| JP | 60178362 A | * | 9/1985 | |
| JP | 05034334 A | * | 2/1993 | |
| WO | WO 9111977 A | * | 8/1991 | |

* cited by examiner

*Primary Examiner*—Yelena G. Gakh
(74) *Attorney, Agent, or Firm*—Pearne & Gordon LLP

(57) ABSTRACT

A wetness indicator including a pH indicating agent may be a single layer or a multilayer composite. One or more layers of the composite may be used to promote or inhibit environmental fluid contact with the pH indicating agent dispersed within at least a portion of a layer thickness. Fluid travel through the layer thickness may be achieved by layer microporosity and/or addition of fluid regulating additives to the layer. The layer or layers may be polymer layers, ink layers, fibrous layers or combinations thereof. Ink compositions for use making such indicators are also disclosed.

13 Claims, 2 Drawing Sheets

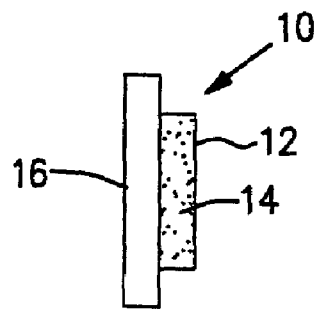
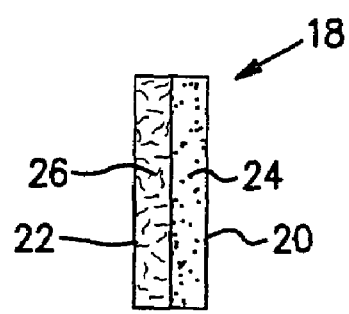
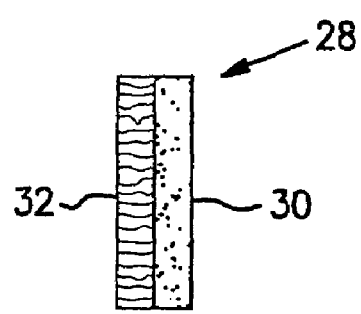
FIG. 1   FIG. 2   FIG. 3
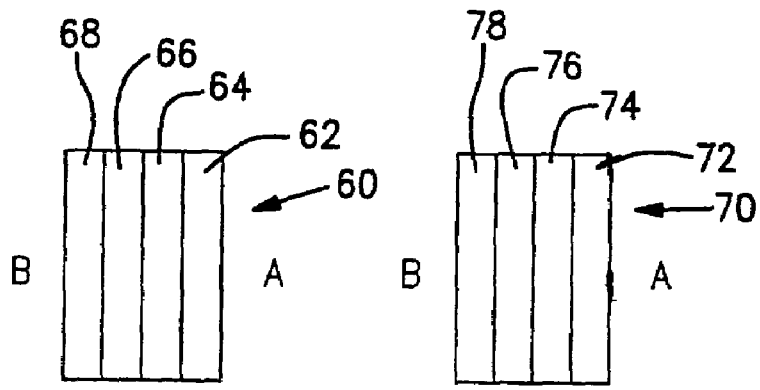
FIG. 4   FIG. 5

WETNESS INDICATOR

This application claims the priority of U.S. Provisional Patent Application No. 60/456,578, filed Mar. 24, 2003, the disclosure of which is incorporated by reference herein.

BACKGROUND OF THE INVENTION AND RELATED ART

The present invention relates to wetness indicators and, more particularly, to indicator composites incorporating pH indicating agents and to compositions that may be used to make such indicator composites. The indicators may be of a single layer or multiple layer composite, and they may be incorporated in articles and devices wherein it is desirable to sense pH, moisture or wetness.

Chemical compounds that change color with change in pH are well-known in the art. The use of such compounds, or so-called pH indicating agents, to provide pH and wetness indications is also known.

Such wetness indicators are frequently used in connection with disposable diapers. For example, U.S. Pat. No. 3,675,654 includes a translucent backing sheet and an indicating agent applied to an absorbent pad surface adjacent the backing sheet which becomes visible upon moisture contact. U.S. Pat. No. 3,731,685 utilizes capillary action to transmit interior diaper moisture along a strip to an exterior end of the strip having an indicator agent. The pH indicating agent is incorporated in a latex adhesive applied to the backing sheet or adjacent pad surface of a disposable diaper in U.S. Pat. No. 4,231,370. It is also known to incorporate indicating agents in hot melt adhesives used in diapers as disclosed in U.S. Pat. Nos. 4,743,238, 5,035,691, 5,066,711 and 5,089,548. In U.S. Pat. No. 5,354,289, such a hot melt adhesive strip is isolated from the diaper interior by a water impervious baffle that extends beyond the adhesive strip dimensions to cause liquid to flow around the edges of the baffle in order to contact the indicator agent and thereby provide a capacity monitor.

Wetness indicators not using pH indicating agents are also used in disposable diaper constructions to provide visible indicia of diaper wetness. These include water soluble dyes rendered visible by contact with diaper liquid in U.S. Pat. No. 3,675,654. An opposite approach is used in U.S. Pat. No. 4,022,211 wherein the indicia is visible if dry, but dispersed upon diaper wetting. In other approaches, visibility masks are removed by diaper wetting to allow viewing of the wetness indicia as in U.S. Pat. Nos. 4,192,311 and 4,705,513.

As distinguished from wetness indicators not using pH indicating agents, the present invention contemplates the use of a pH indicating agent for pH or wetness indication of an environment. Herein, an environment comprises a moisture containing fluid. The fluid may be present in liquid and/or in condensable vapor form.

SUMMARY OF THE INVENTION

It has now been discovered that pH indicating agents may be utilized more effectively with fluid regulation or control in single layer and multiple layer wetness indicators within a desired timeframe of use. Fluid control may be used to promote or to inhibit fluid contact with the pH indicating agent as well as to limit the diffusion of the latter.

As used herein, fluid regulation includes one or more of the following. (i) Moisture transmission or absorption enabling controlling or regulating the amount of fluid contacting the surface or flowing into the body of one or more layers of the indicator. (ii) Obstructing or preventing the bleed of indicator back into the environment. In preferred embodiments, fluid regulation includes both moisture transmission and bleed prevention.

The invention contemplates a controlled pathway for fluid which comprises moisture and/or other pH contributing species such as acids or alkali ions in a water phase to be transported to the surface of the indicating layer or into its body for indication. The extent of transport of fluid is regulated to be representative of the extent of wetness in the environment or to its pH level. A pathway for indicating agent back into the environment may also result as a consequence of creating this pathway for moisture into the indicator body. A preferred embodiment would be the use of barrier layers or fluid regulating additives that are moisture absorbing or transmitting resins, which allow for transmitting moisture in one direction but also prevent bleed in the reverse direction within the contemplated fluid regulation herein.

In the illustrated embodiments, fluid regulation is provided through at least a portion of the thickness of a layer of the wetness indicator in order to contact the pH indicating agent. Also illustrated is an ink for constructing such layers with said transmission. Typically, the wetness indicator has a surface exposed to the fluid and at least a portion of the wetness indicating agent is contained within a layer for contact with the fluid following transmission of the fluid through the layer.

The fluid regulating additive, or at least a portion thereof, may be incorporated in one or more layers of the wetness indicator to enable control of the fluid contacting the pH indicator. To that end, the layer containing the pH indicator may have sufficient microporosity and/or moisture vapor transmission rate (MVTR) to achieve fluid penetration to contact the pH indicator or a moisture transmitting additive may be incorporated in at least the portion of the thickness of the layer to achieve fluid contact with the pH indicating agent therein.

Suitable pH indicating agents are well known in the art and include cresol red, thymol blue, methyl yellow, methyl orange, bromophenol blue, bromocresol green, methyl red, p-Nitrophenol, phenol red, phenophthalein and Alizarin yellow R. These agents are commercially available from numerous suppliers such as Neha Chemicals.

Suitable fluid regulating additives include commercially available superabsorbent polymers, typically polyacrylates, available from Dow Chemical, BASF (HYSORB brand), Degussa AG (FAVOR brand). Cellulose and cellulosic derived resins, such as METHOCEL brand from Dow Chemical, may also be used as additives. Anhydride resins such as maleic anhydride or nadic methyl anhydride or SMA brand resins form Sartomer Company are also useful. Polyolefin blended resins, such as INTERACT 91-04365 available from ONeil Color, suitable for blending with other plastics during extrusion, may be used. Synthetic zeolites such as Zeolum Series by Tosoh may be used. Zeolites with controlled pore size openings have an added benefit of acting as barriers that allow the forward flow of moisture due to the smaller molecular size of water into the indicator while obstructing the reverse flow of pH indicating agents (larger molecular size) back into the environment. Other suitable additives may comprise typical desiccants such as silica gel, calcium oxide, clays and calcium sulfate may be used.

As noted above, preferred embodiments of the invention contemplate fluid regulation including fluid transmission to the pH indicating agent and inhibiting of bleed of the agent into the fluid. Zeolites with selected pore opening sizes allow for both mechanisms.

The wetness indicator may comprise a single layer wherein both pH indication and fluid control occur. For example, in the illustrated embodiments, a single layer may be provided with a microporosity or moisture vapor transmission rate sufficient to enable fluid penetration and contact with pH indicating agent disposed within at least a portion of the thickness of the layer.

The wetness indicator may comprise a multiple layer composite wherein pH indication and fluid control occur in separate layers, or in both layers. In the illustrated embodiments, the layer providing fluid control is disposed between the environment and the layer containing the pH indicating agent.

In accordance with the invention, a layer may comprise or be in the form of a polymer layer, an ink or coating layer, or a fibrous layer or mixtures thereof. The layer may be continuous or discontinuous. A composite may include similar or different types of layers. Further, a composite may include a matrix which is a structure that allows for a dispersed phase.

The polymer layer may be a substantially continuous film of polymer that is impermeable to the fluid. Alternatively, the polymer layer may have a microporosity or a sufficient MVTR, in at least a portion of its thickness, to permit full or partial penetration by the fluid of the environment. The polymer layer may comprise polyolefin based polymers such as polypropylene, films, polyethylene films or other polymers such as polyester, polystyrene, polyvinyl chloride or polyurethane films or composites thereof. Films formed of copolymers, polymer blends and mixtures thereof are also contemplated. An example of a film described above could be biaxially oriented polypropylene film.

Suitable porosities defined in terms of pore opening size are 1 micron to 150 microns pore size and useful MVTR range from 0.5 g/100 sqin/24 hr to 25,000 g/100, and more preferably, from 1,500 to 15,000, and most preferably, from 2,500 to 8,000 sqin/24 hr as measured by ASTM E98.

In flexible indicator applications, useful polymer layers may have a weight as low as 2 grams/meter$^2$ (gsm) and up to about 105 gsm and, more preferably, in the range of from 6 to 45 gsm. The thickness of the polymer layer may range from a fraction of a mil up to about 6 mils.

The desired fluid penetration of the polymer layer may be provided by a moisture transmitting additive dispersed in at least a portion of the polymer. The moisture transmission rate may be selected in accordance with a particular application. Useful transmission rates are 0.5 g/100 sqin/24 hr to 25,000 g/100 sqin/24 hr.

In the illustrated embodiments, the moisture transmitting additive comprises a fluid regulating additive as noted above. The fluid regulating additives may be dispersed throughout the layer thickness or in selected portions of the layer. The additive may be used in amounts ranging from 1% to 35% based on the weight of the layer components, and more preferably, with better performance in the 5% to 25% range, and most preferably, in the 5% to 15% range, depending upon the application.

The moisture transmission or MVTR increases with increasing additive concentration and results in decreased or shorter time for indication by the pH indicating agent. Conversely, the lower the concentration of moisture transmission additive, the lower the moisture transmission or MVTR and the greater the time for indication or response. For example, a single layer composite containing 25% fluid regulating additive and 4% pH indicating agent, when contacted with liquid water may commence substantial indication in less than 30 seconds. The same composite with reduced additive of 10% and 4% indicating agent may require over 50 seconds to substantial indication. In both cases, the composites were exposed to 5 cc of water.

The pH indicating agent may also be dispersed throughout the layer thickness or in selected portions of the layer and/or applied to a surface thereof. The pH indicating agent may be used in amounts ranging from 0.1 to 25% based on the weight of the polymer layer.

The ink or coating layer may be formed of polymers and/or resins, and may therefore differ from a polymer layer in some applications. For convenience herein, reference to an ink layer will be understood to include a coating unless otherwise prohibited by the context. As in the case of a polymer layer, the ink layer may be impermeable to the fluid or permeability may be achieved by microporosity or a fluid regulating additive contained in the ink layer. Layers printed with such inks could be substantially continuous or discontinuous in the form of separated dots as is common with current process print technology.

For flexible indicators, the ink layer may range in weight from 1 to 7 gsm, and have a thickness as low as 0.05 mil to as high as 1 mil. Also, the pH indicating agent may be dispersed in the ink layer thickness in a range of from 0.1 to 25% based on the weight of the ink layer.

Another embodiment of this invention is a pH indicating ink that allows for moisture transmission. The inks could be formulated as solvent based, water based or UV or other radiation curable inks. Water based inks are generally not preferred especially if the purpose of the ink is to indicate the presence of moisture. The indicating agent would be activated by the liquid ink and proper functionality would be dependent on drying the ink completely so that little or no indicating agent would remain activated. Suitable inks would comprise a pH indicating agent and a fluid regulating additive.

BRIEF DESCRIPTION OF THE DRAWINGS

FIG. 1 is a sectional view of a single layer wetness indicator in accordance with the invention;

FIG. 2 is a sectional view of a multiple layer wetness indicator in accordance with the invention;

FIG. 3 is a sectional view of a multiple layer wetness indicator in accordance with another embodiment of the invention;

FIG. 4 is a sectional view of a multiple layer wetness indicator in accordance with another embodiment of the invention;

FIG. 5 is a sectional view of a multiple layer wetness indicator in accordance with another embodiment of the invention;

DETAILED DESCRIPTION OF THE DRAWINGS

Figure 6:
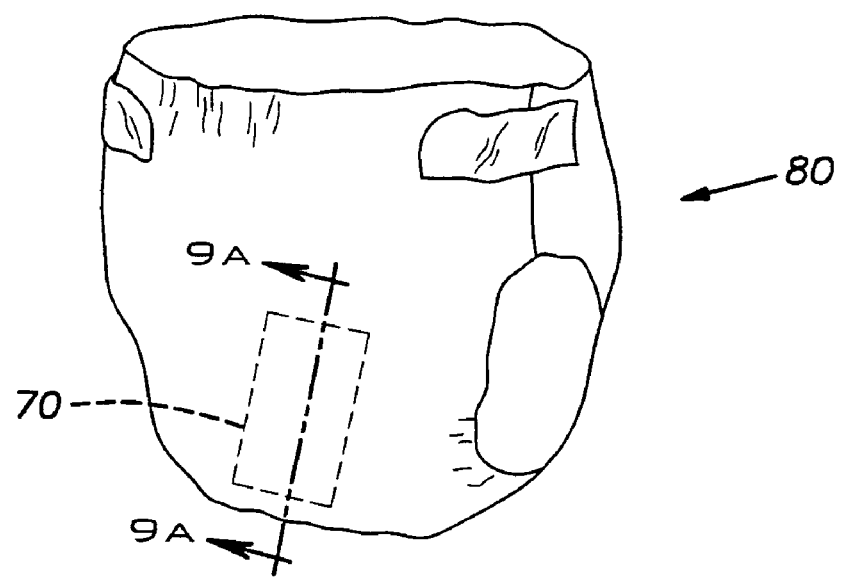
FIG. 6 is a perspective view showing a disposable diaper having the wetness indicator arranged therein to indicate diaper wetness.

Referring to FIG. 1, a single layer wetness indicator 10 is provided by a microporous polymer layer 12 containing dispersed pH indicating agent 14. For example, a polypropylene film having adequate fluid diffusion properties may be blended with Thymol Blue as the pH indicating agent. In this manner, the polypropylene provides a polymer matrix having the indicating agent dispersed therein.

The indicator 10 is disposed adjacent a transparent wall portion 16 of a food packaging container (not shown). For example, the food container may be a flexible bag container for potato chips, and the indicator 10 would indicate staleness or an undesirable level of moisture within the container. The indicator 10 may be mounted to the wall portion 16 by a translucent or transparent adhesive, or it may be otherwise retained adjacent wall portion 16 with all surfaces thereof exposed to the environment.

In this instance, the sensed environment comprises fluid within the interior of the container and excessive levels of moisture are identified by the indicator 10. In such an application, it may be preferred to use an indicator having a high MVTR range since diffusional resistance to flow of moisture vapor into the indicator should be minimized.

The incorporation of pH indicating agent into the thickness of the layer with fluid penetration to reach the agent provides several advantages in accordance with the invention. In the absence of fluid penetration, the prior art incorporation of pH indicating agent into the thickness of the layer results in a substantial portion of the agent being isolated from contact with the fluid and therefore rendered ineffective. Accordingly, fluid penetration in accordance with the invention enables a reduced amount of pH indicating agent to the used and a reduced amount of bleed of the agent into the environment while achieving a similar response level as compared with the prior art.

Further, the use of a fluid barrier layer or moisture transmitting resins such as ZEOLUM reduce the bleed of indicator into the environment by providing hindrance to the migration of the agent. While steric hindrance is inherent to any polymer mixture, these embodiments are particularly effective in reducing bleed. The barrier layer could function as an external wall of obstruction, the thickness of which would increase the resistance to migration of the agent whereas the use of zeolite resins provide a means to entrap the indicating agent thereby minimizing its bleed into the environment. These embodiments are particularly useful in allowing formulators more freedom in choosing components for wetness indicating layers. These embodiments are also useful in helping preserve the definition of graphics that are comprised of such composites.

Referring to FIG. 2, a multiple layer wetness indicator 18 comprises multiple layer composites formed by a pH indicating layer 20 and a fluid barrier layer 22. An indicating agent 24 is dispersed in the layer 20 and, for example, this layer and indicating agent may be the same as in the layer 14 of the embodiment of FIG. 1.

The fluid barrier layer 22 contains a fluid regulating additive 26 dispersed therein to provide the desired degree of moisture transmission. For example, the layer 22 may be formed of polyethylene and the fluid regulating additive 26 may comprise superabsorbent polymer dispersed in a polypropylene matrix. The relative amount of fluid regulating additive 26 may be selected in accordance with the concentration or level of fluid present in the environment and whether the fluid is present in a relatively high diffusible liquid species or a relatively low diffusible vapor species. Also, increased amounts of fluid regulating additive will result in increased fluid transmission and affect the desired response time. Accordingly, specific concentrations of fluid regulating additive will depend upon the application.

Referring to FIG. 3, a wetness indicator 28 comprises a multiple layer composite of a pH indicating layer 30 and a fluid barrier layer 32. The layer 32 may be formed of the same polymer as layer 24 described above. In this embodiment, the layer 32 has a microporosity sufficient to transfer fluid from the environment through its thickness for contact with the pH indicating layer 30. Accordingly, it is not necessary to add a separate fluid regulating additive. Of course, a polymer of lesser microporosity may have a fluid regulating additive added to it.

It should be appreciated that each of the wetness indicators described above may be provided in the form of a polymer layer or a printed ink layer. Further, the microporosity of the layers enables the fluid or moisture to penetrate deeper into the layer or layers, based upon the amount of fluid present in the environment. Accordingly, multiple layers may each have a different pH indicating agent and response or different concentration and intensity of response. In this manner, the layers may be arranged to provide for indication of threshold levels and/or different degrees of wetness or fluid in the environment.

Referring to FIG. 4, a wetness indicator 60 comprises a multiple layer composite formed by layers 62, 64, 66 and 68. Each of the layers 62, 64 and 66 may include differing amounts of pH indicating agents or different pH indicating agents. In addition, each of the layers 62, 64 and 66 provides sufficient microporosity or MVTR to allow penetration by the fluid of the environment and contact with the pH indicating agents. The degree of fluid penetration will be proportional to the fluid concentration or level in the environment. The layer 68 is a clear or transparent layer.

Further, the wetness indicator 60 may be arranged so that, depending on the side of view A or B, the layers 62, 64 and 66 could become opaque, transparent, change color, or expose or hide graphics as indicators for the degree of wetness.

Referring to FIG. 5 a wetness indicator 70 comprises a three layer composite including a protective layer 72, an indication layer 74 and a barrier and anchorage layer 76. The indication layer 74 comprises a layer of pH indicating printing ink. The layer 76 secures the composite 70 to a substrate 78. In this composite, the barrier layer 72 prevents the indicating agent dye from flowing or dissipating into the surrounding fluid environment, but does allow for the passage of fluid to the indication layer. Such a layer may consist of any ink that is somewhat transparent to allow for visual indication in viewing from side A. Such an ink layer may also consist of polymers and/or resins that allow for absorption, transmission of moisture and fluid to allow the indicating layer to come into fluid contact and be activated. The degree of saturation or penetration of fluid in this layer enables differential indication. The layer 76 may be present as a barrier anchorage layer that is applied to the substrate 78 prior to applying the indicating layer 74. The function of the layer 76 may include allowing for visual indication from side B, assisting in anchoring the layer 74 to the substrate 78 and further sealing the adjacent side of the indication layer 74 so that activation can only occur from one side.

Figure 6A:
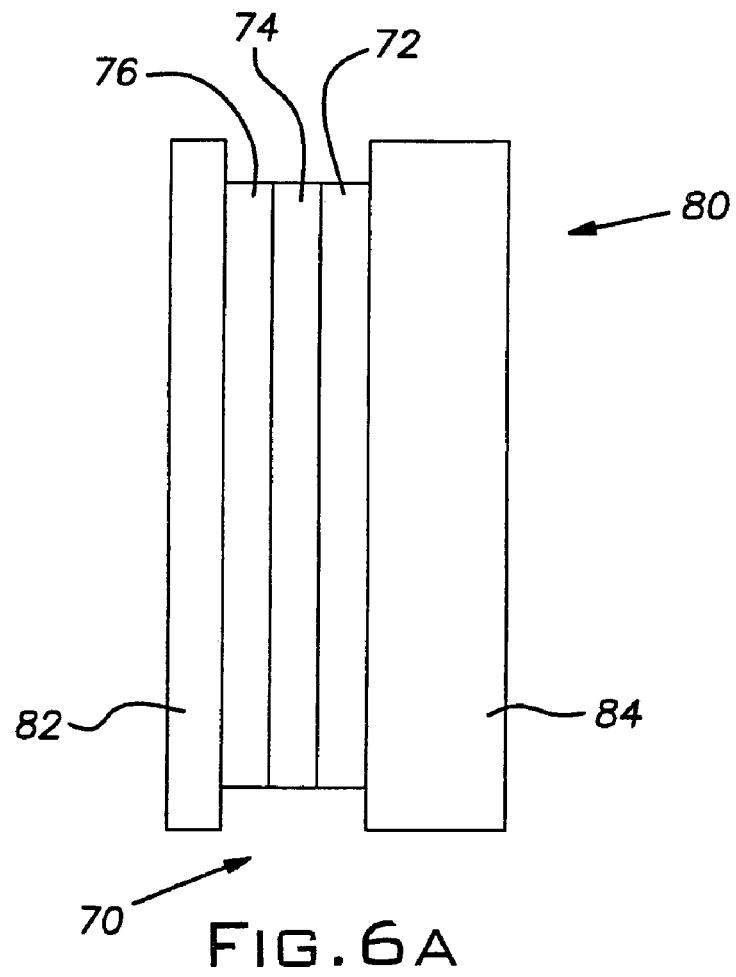
FIG. 6A is a fragmentary sectional view, on an enlarged scale, showing the wetness indicator incorporated in the disposable diaper of FIG. 6.

Referring to FIGS. 6 and 6A, a disposable diaper 80 is shown. The diaper 80 includes a water impervious backing sheet 82 and absorbent pad 84 which may include an absorbent fiber layer as well as a facing sheet which would contact a user's skin. The composite 70 is secured to the inside surface of the backing sheet 82 by the barrier anchorage layer 76. The layer 76 is substantially transparent so that indication layer 74, upon contact with the urine or fluid environment of the diaper, will be visible through the backing sheet 82.

The barrier layer 72 also prevents premature activation of the pH indicating agent due to moisture present in the diaper during storage and prior to use. Thus, the microporosity and/or MVTR of the barrier layer may be selected to prevent fluid contact of the pH indicating agent by such moisture.

The indicating layer 74 includes a pH indicating agent that may be arranged to provide a graphic design or message. Also, the pH indicating agent may be translucent or substantially not visible through the backing sheet 82 prior to fluid contact. Accordingly, the fluid contact activates the pH indicating agent to provide a graphic message.

Of course, the diaper 80 may comprise any urinary incontinence article, sanitary napkin, a bandage or a like article. In addition to such personal wear articles, the wetness indicators may be used in an environment to be monitored for moisture. For example, the wetness indicator may be secured to a viewing window of a home clothes dryer.

One or more composite layers may be formed from curing pH indicating inks. The layers may be in the form of films or discontinuous dots dependent on the graphic desired. Inks can be compounded with carriers that are solvents or water where cure occurs in general by drying off the carrier. Inks can also be compounded to be substantially solvent or water free and cured by exposure to UV light or other appropriate radiation sources. UV inks and solvent inks are preferred embodiments. Water based inks tend to have some residual moisture after drying and the resin components tend to have a pH value which is imparted to the ink composition both of which may render portions prematurely activated. UV and solvent inks do not have a pH.

The following ink formulations are illustrative of useful inks in accordance with the invention.

Formulation 1 UV Cured—Without Fluid Regulating Additive

| Ingredient | Weight % |
| --- | --- |
| Photomer 4094 (Cognis) | 28-40 |
| Photomer 5429 (Cognis) | 28-40 |
| Photomer 4967 (Cognis) | 8-13 |
| Texaphor 3241 (Cognis) | 1-5 |
| Photomer 51 (Cognis) | 1-5 |
| Irgacure 369 (Ciba) | 1-4 |
| Bromo Cresol Green | 0.5-12 |

Formulation 2 UV Cured-With Fluid Regulating Additive

| Ingredient | Weight % |
| --- | --- |
| Photomer 4094 (Cognis) | 28-40 |
| Photomer 5429 (Cognis) | 28-40 |
| Photomer 4967 (Cognis) | 8-13 |
| Texaphor 3241 (Cognis) | 1-5 |
| Photomer 51 (Cognis) | 1-5 |
| Irgacure 369 (Ciba) | 1-4 |
| Bromo Cresol Green | 3-8 |
| METHOCEL (Dow) | 0.5-8 |

Formulation 3 Solvent Based-Without Fluid Regulating Additive

| Ingredient | Weight % |
| --- | --- |
| Vinavil K40 (Cognis) | 15-30 |
| Dow Corning Z 6011 | 1-5 |
| Rewopol SBD075 | 0.2-08 |
| N Propyl alcohol | 40-55 |
| Ethyl acetate | 10-20 |
| Bromo Cresol Green | 0.5-12 |

Formulation 4 Solvent Based-With Fluid Regulating Additive

| Ingredient | Weight % |
| --- | --- |
| Vinavil K40 (Cognis) | 15-30 |
| Dow Corning Z 6011 | 1-5 |
| Rewopol SBD075 | 0.2-0.8 |
| N Propyl alcohol | 40-55 |
| Ethyl acetate | 10-20 |
| Bromo Cresol Green | 3-8 |
| METHOCEL (Dow) | 0.5-8 |

The foregoing formulations may be modified at specific components and composition percentages, and they are merely provided as being illustrative of useful pH indicating ink compositions.

The resins used to provide a body or a binder for the matrix in the inks include polymers of acrylates, alkyd resins, amides, amino resins, ethylene co-terpolymer resins such as EVA, epoxy resins, fluoropolymers, hydrocarbon resins, phenols, polyesters, olefins, polyurethanes, silicone, polystyrene and polyvinyls.

While particular embodiments of the present invention had been illustrated and described, it would be obvious to those skilled in the art and various other changes and modifications can be made without departing from the spirit and scope of the invention. It is intended to cover in the appended claims all such changes modifications that are within scope of this invention.

What is claimed:

1. A personal wear absorbent article in combination with a wetness indicator to be exposed to an environment to monitor the presence of a fluid in the environment, said wetness indicator comprising a multiple layer composite of a first ink layer applied to a second ink layer, said first ink layer being disposed at least in part between said environment and said second ink layer to control fluid contact with at least a portion of the second ink layer, said second ink layer containing a pH indicating agent that provides a visual indication in response to contact with said fluid and at least one of said layers containing a fluid regulating additive to regulate fluid contact with said pH indicating agent in said second ink layer, said fluid regulating additive being selected from the group consisting of silica gel, superabsorbent polymers, cellulosic resins, anhydride resins, polyolefin blend resins, zeolites, calcium oxide, clays and calcium sulfate.

2. The combination as in claim 1, wherein said composite is part of an absorbent article worn on a user's body.

3. The combination as in claim 1, wherein said fluid regulating additive is a zeolite, said fluid comprises molecules of a first size and said pH indicating agent comprises molecules of a second size larger than said first size, said zeolite having a pore size that allows the flow of fluid therethrough but obstructs the flow of said pH indicating agent contacted by said fluid to thereby reduce bleed of said pH indicating agent from said second ink layer.

4. The combination as set forth in claim 1, wherein said first ink layer is impermeable to said fluid is a discontinuous layer, and thereby prevents fluid contact with said portion of said second ink layer.

5. The combination as set forth in claim 4, wherein said discontinuous first ink is in the form of separated dots.

6. The combination as set forth in claim 1, wherein said first ink layer is microporous and thereby lessens and/or delays fluid contact with said portion of said second ink layer.

7. The combination as set forth in claim 1, wherein both said first and second ink layers each contain fluid regulating additive.

8. The combination as set forth in claim 1, wherein said second ink layer is a substantially continuous film of polymer having said pH indicating agent and fluid regulating additive dispersed therein.

9. The combination as set forth in claim 1, wherein said first and second ink layers each have a weight of from about 2 gsm to about 105 gsm and a thickness of from about a fraction of a mil to about 6 mils.

10. The combination as set forth in claim 1, wherein said second ink layer contains from about 0.1% to about 25% of said pH indicating agent based on the weight of the second ink layer.

11. The combination as set forth in claim 1, wherein said fluid regulating additive is a zeolite having a pore opening size that restricts the passage of a molecule larger than a water molecule.

12. The combination as set forth in claim 1, wherein said first and second ink layers each comprise a substantially continuous film of polymer having a weight of from about 2 gsm to about 105 gsm and a thickness of from about a fraction of a mil to about 6 mils, said second ink layer contains from about 0.1% to about 25% of said pH indicating agent based on the weight of said polymer forming said second ink layer, and said fluid regulating additive is dispersed in at least one of said ink layers.

13. The combination as set forth in claim 12, wherein said fluid regulating additive is a zeolite having a pore opening size that permits the flow of fluid into said second ink layer to contact said pH indicating agent and restricts the flow of said pH indicating agent contacted with said fluid from said second ink layer into said environment.

* * * * *